US009254136B2

(12) United States Patent
Ye et al.

(10) Patent No.: US 9,254,136 B2
(45) Date of Patent: Feb. 9, 2016

(54) DRILL HEAD LOCKING APPARATUS AND DRILL HEAD

(75) Inventors: Lei Ye, Chongqing (CN); Jian Zhou, Chongqing (CN); Hua Feng, Chongqing (CN); Fei Li, Chongqing (CN); Hengyang Zhu, Chongqing (CN); Congxiao Li, Chongqing (CN)

(73) Assignee: Chongqing Runze Pharmaceutical Co., Ltd., Chongqing (CN)

(*) Notice: Subject to any disclaimer, the term of this patent is extended or adjusted under 35 U.S.C. 154(b) by 409 days.

(21) Appl. No.: 13/823,087

(22) PCT Filed: Aug. 24, 2011

(86) PCT No.: PCT/CN2011/078809
§ 371 (c)(1), (2), (4) Date: Mar. 13, 2013

(87) PCT Pub. No.: WO2012/041132
PCT Pub. Date: Apr. 5, 2012

(65) Prior Publication Data

US 2013/0178857 A1 Jul. 11, 2013

(30) Foreign Application Priority Data

Sep. 30, 2010 (CN) .......................... 2010 1 0298087

(51) Int. Cl.
*B23B 31/107* (2006.01)
*A61B 17/16* (2006.01)
*B23B 31/10* (2006.01)

(52) U.S. Cl.
CPC ............... *A61B 17/162* (2013.01); *B23B 31/10* (2013.01); *B23B 31/1071* (2013.01); *A61B 17/1695* (2013.01); *Y10S 279/905* (2013.01); *Y10T 279/17* (2015.01); *Y10T 279/17145* (2015.01); *Y10T 279/17196* (2015.01); *Y10T 279/17743* (2015.01); *Y10T 279/17752* (2015.01)

(58) Field of Classification Search
CPC .......................... B23B 31/107; B23B 31/1071
USPC .................... 279/30, 22, 74, 75, 82, 905, 904
See application file for complete search history.

(56) References Cited

U.S. PATENT DOCUMENTS

| | | | | |
|---|---|---|---|---|
| 4,199,160 A * | 4/1980 | Bent | ............................... | 279/30 |
| 4,692,073 A * | 9/1987 | Martindell | ................ | 408/239 A |
| 5,505,737 A * | 4/1996 | Gosselin et al. | ................ | 606/79 |
| 5,989,257 A * | 11/1999 | Tidwell et al. | .................. | 606/79 |
| 6,554,290 B2 * | 4/2003 | Lin | ................................ | 279/72 |
| 2003/0163134 A1 * | 8/2003 | Riedel et al. | .................... | 606/79 |
| 2005/0116429 A1 * | 6/2005 | Chang | ............................ | 279/75 |

FOREIGN PATENT DOCUMENTS

DE 4103663 A1 * 8/1992 ............ A61B 17/16

* cited by examiner

*Primary Examiner* — Eric A Gates
*Assistant Examiner* — Chwen-wei Su

(57) ABSTRACT

A drill head locking apparatus and a drill head are provided. The locking apparatus includes a protruding platform having a through hole, a bearing on the inner wall of a small cylinder on the protruding platform, a locking sleeve fitted on the protruding platform, and a protrusion arranged on the upper part of the inner wall of the locking sleeve. The lower part of the inner wall of the locking sleeve is a conical face. A spring is arranged between the bottom face of the conical face and an upper bottom face of the protruding platform. A press plate is connected with a screw thread on the outer wall of the top part of the small cylinder on the protruding platform and presses down on the protrusion. A conical hole is arranged on the wall of the small cylinder and communicates with the through hole of the protruding platform.

8 Claims, 2 Drawing Sheets

18
7
6
5
4
3
2
16
1
17
13
8
12
11
8
9
10
15
14
13

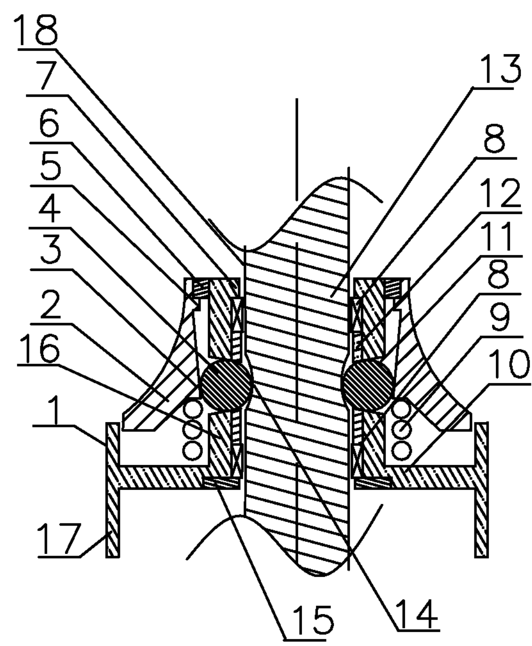
F I G. 1

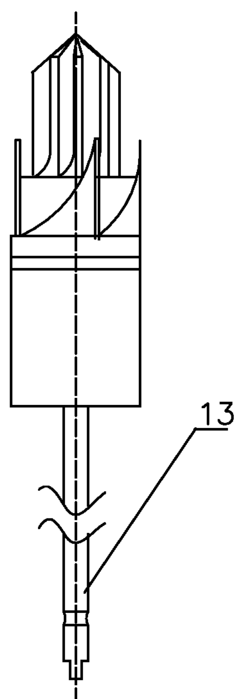
F I G. 2

DRILL HEAD LOCKING APPARATUS AND DRILL HEAD

BACKGROUND OF THE INVENTION

1. Field of the Invention

The present invention relates to a bone drill machine for surgery, and more particularly to a drill head locking apparatus and a drill head.

2. Description of the Prior Art

During a surgical operation, skull drills, milling cutters and milling drills are often used to open a skull. The skull drill comprises a main machine, a speed reducer, a locking seat and a drill head. The drill head comprises a front blade portion and a rear transmission rod. The locking seat is threadedly connected to the front of the speed reducer. The drill head is inserted through the locking seat and connected with the power output of the speed reducer. The function of the locking seat is to engage with the transmission rod, preventing the drill head from disengagement during working. The existing locking apparatus provides engaging hooks to lock. It is inconvenient for installation and not easy for use.

Accordingly, the inventor of the present invention has devoted himself based on his many years of practical experiences to solve these problems.

SUMMARY OF THE INVENTION

The primary object of the present invention is to provide a drill head locking apparatus and a drill head for convenient use.

In order to achieve the aforesaid object, the drill head locking apparatus comprises a protruding platform having a through hole, a bearing arranged on the inner wall of a small cylinder on the protruding platform, and a locking sleeve fitted on the protruding platform. The locking sleeve has a protrusion arranged on the upper part of the inner wall of the locking sleeve. The lower part of the inner wall of the locking sleeve is a conical face. A spring is provided between a bottom of the conical face and an upper bottom face of the protruding platform. A press plate is threadedly connected to an outer wall of the top part of the small cylinder on the protruding platform and presses the protrusion. A conical hole is arranged on the wall of the small cylinder on the protruding platform and communicates with the through hole of the protruding platform. A steel ball is arranged in the conical hole.

For the transmission rod to be applied with even force, the drill head locking apparatus comprises two bearings respectively located under the outer wall and above the upper bottom face.

For firmness of the two bearings, a support member is provided between the two bearings.

For convenient connection of a speed reducer, the inner wall of a big cylinder under the protruding platform has inner threads.

A drill head to mate with the aforesaid drill head locking apparatus comprises a front blade portion and a rear transmission rod. The transmission rod has a recess thereon.

When it is necessary to insert the transmission rod, the locking sleeve is pressed down. At this moment, the conical face is moved down and the steel ball rolls outward. After the transmission rod reaches a desired position, the locking sleeve is released. Through the spring, the locking sleeve ascends and the conical face holds against the steel ball to move inward to engage with the recess of the transmission rod in order to position the transmission rod. The drill head locking apparatus and the drill head are easy and convenient to operate, lock firmly, and offer an improved safety.

BRIEF DESCRIPTION OF THE DRAWINGS

FIG. 1 is a sectional view showing the drill head locking apparatus according to a preferred embodiment of the present invention; and FIG. 2 is a schematic view showing the drill head according to the preferred embodiment of the present invention.

DETAILED DESCRIPTION OF THE PREFERRED EMBODIMENTS

Embodiments of the present invention will now be described, by way of example only, with reference to the accompanying drawings.

As shown in FIG. 1 and FIG. 2, a drill head comprises a front blade portion and a rear transmission rod (13). The transmission rod (13) has a recess (14) thereon. A drill head locking apparatus includes a protruding platform (1) having a through hole and a bearing (8) arranged on an inner wall of a small cylinder on the protruding platform (1). In this embodiment, the drill head locking apparatus comprises two bearings (18) respectively located under an outer wall (7) and above an upper bottom face (10). A support member (12) is provided between the two bearings (8). The two bearings (8) can effectively ensure stability of the transmission rod and decrease heat when rotating. The upper bottom face (10) is threadedly connected with a tightening member (15) to hold against the bearings (8) and the support member (12) so as to enhance firmness of the bearings (8). A locking sleeve (2) is fitted on the protruding platform (1). The locking sleeve (2) has a protrusion (5) arranged on an upper part of an inner wall of the locking sleeve (2). A lower part of the inner wall of the locking sleeve (2) is a conical face (3). A spring (9) is provided between a bottom of the conical face (3) and the upper bottom face (10) of the protruding platform (1). A press plate (6) is threadedly connected to the outer wall (7) of the top part of the small cylinder on the protruding platform (1) and presses the protrusion (5). A conical hole (11) is arranged on the wall of the small cylinder on the protruding platform (1) and communicates with the through hole of the protruding platform (1). A steel ball (4) is arranged in the conical hole (11). The conical hole (11) corresponds in position to the recess (14) of the transmission rod (13) of the drill head. An inner wall of a big cylinder under the protruding platform (1) has inner threads. In this embodiment, the number of the conical holes (11) and the steel balls (4) is two as an equivalent change. The number can be three for a better locking effect.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A drill head locking apparatus, mating with a drill bit, comprising the drill bit, comprising a transmission rod (13) having a recess (14) thereon, with the transmission rod (13) housed in a through hole (18) of a constant diameter H both at one end and at another end thereof in such a way that both an upper part and a lower part of the transmission rod (13) communicates with an open air, and a middle part thereof being sleeved by the locking apparatus, a protruding platform (1) including a small cylinder (16), a steel ball (4), a press plate (6), an outer wall (7), disposed next to the transmission rod (13), one or more spring (9), an upper bottom face (10), a conical hole (11), corresponding, in position to the recess (14), for the locking apparatus to be fixed around the transmission rod (13), a tightening member (15), two bearing (8) separately arranged on an inner wall of the small cylinder (16) on the protruding platform (1), each abutting against one of two support members (12) as wells as against the steel ball (4), and a locking sleeve (2) fitted on the protruding platform (1), with the locking sleeve (2) concave inwards, the locking sleeve (2) having a protrusion (5) uniformly protruding towards the outer wall (7) and the transmission rod (13) in a same direction on an upper part of an inner wall of the locking sleeve (2), a lower part of the inner wall of the locking sleeve (2) being a conical face (3) with an inner wall linearly slanting towards the steel ball (4), the one or more spring (9) being provided between a bottom of the conical face (3) and an upper bottom face (10) of the protruding platform (1), through which the locking sleeve (2) ascends and the conical face (3) abuts against the steel ball (4) to move inward in engagement with the recess (14) and position the transmission rod (13), a press plate (6) being threadedly connected to the outer wall (7) of a top part of the small cylinder (16) on the protruding platform (1) and pressing against the protrusion (5), a conical hole (11) being arranged on a wall of the small cylinder (16) on the protruding platform (1) and communicating with the through hole (18) of the protruding platform (1), the steel ball (4) being arranged in the conical hole (11), wherein the locking sleeve (2) is configured to be pressed down to compress the springs (9) to disengage the steel ball (4) from the conical face (3) for rolling outwards away from the transmission rod (13) upon meeting the transmission rod (13) to position the transmission rod (13);

once the transmission rod (13) reaches a desired position, the locking sleeve (2) is released and ascends through a restoration force of the springs (9), and the conical face (3) abuts against the steel ball (4) for rolling inwards to engage with the recess (14).

2. The drill head locking apparatus as claimed in claim 1, wherein the two bearings (8) respectively located under the outer wall (7) and above the upper bottom face (10).

3. The drill head locking apparatus as claimed in claim 2, wherein each of the two support members (12) is provided between the two bearings (8).

4. The drill head locking apparatus as claimed in one of claims 1 to 3, wherein an inner wall of a big cylinder (17) under the protruding platform (1) has inner threads.

5. A drill head to mate with the drill head locking apparatus as claimed in claim 4, further comprising a front blade portion.

6. A drill head to mate with the drill head locking apparatus as claimed in claim 3, further comprising a front blade portion.

7. A drill head to mate with the drill head locking apparatus as claimed in claim 2, further comprising a front blade portion.

8. A drill head to mate with the drill head locking apparatus as claimed in claim 1, comprising a front blade.

* * * * *